United States Patent [19]
Ohyagi

[11] Patent Number: 5,903,335
[45] Date of Patent: May 11, 1999

[54] APPARATUS FOR DISPLAYING VISUAL ACUITY CHART WITH CONSTANT MAGNIFICATION

[75] Inventor: Wataru Ohyagi, Tokyo, Japan

[73] Assignee: Kabushiki Kaisha Topcon, Tokyo, Japan

[21] Appl. No.: 08/876,354

[22] Filed: Jun. 25, 1997

[30] Foreign Application Priority Data

Jun. 28, 1996 [JP] Japan .................................. 8-169916

[51] Int. Cl.$^6$ ........................................................ A61B 3/02
[52] U.S. Cl. .......................... 351/237; 351/239; 351/243
[58] Field of Search .................................... 351/222, 237, 351/239, 243, 244, 216

[56] References Cited

U.S. PATENT DOCUMENTS 5,255,027  10/1993  Reiner et al. ............................ 351/239

Primary Examiner—Huy Mai
Attorney, Agent, or Firm—Oppedahl & Larson LLP

[57] ABSTRACT

In an apparatus for displaying a visual acuity chart table, in response to the change of the distance between an eye to be examined and an apparatus body, a concave mirror of a visual chart optical system is moved along a desired optical axis direction and a concave lens is inserted in the optical path of the visual chart optical system, so that the forming magnification of the visual chart images of various kinds of visual charts is kept constant. Thus, irrespective of the distance between the eye to be examined of a person to be examined and the apparatus body, the visual chart images of the visual charts having a constant size can be displayed to the eye E to be examined at a constant distance, and an accurate eye examination to the eye to be examined is carried out irrespective of the dimensions of an eye examination space.

8 Claims, 8 Drawing Sheets

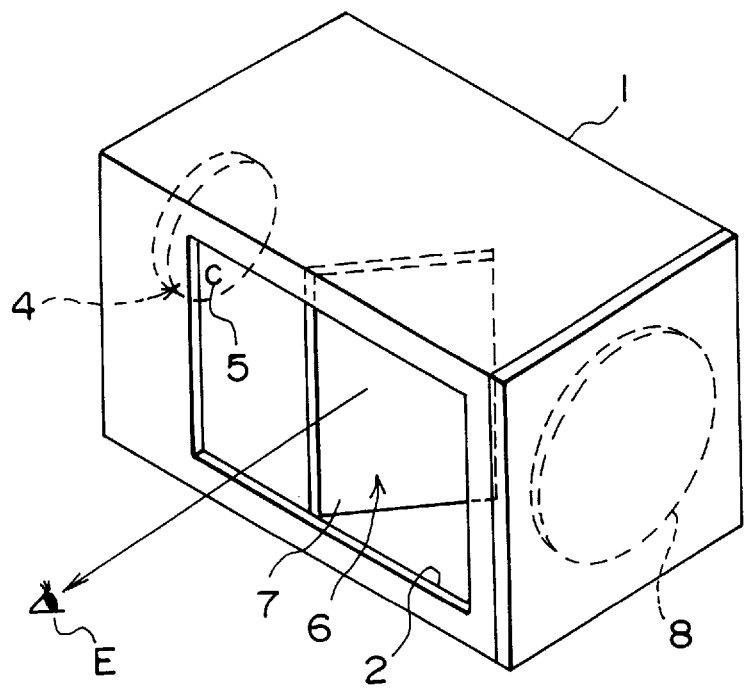
F I G . 1
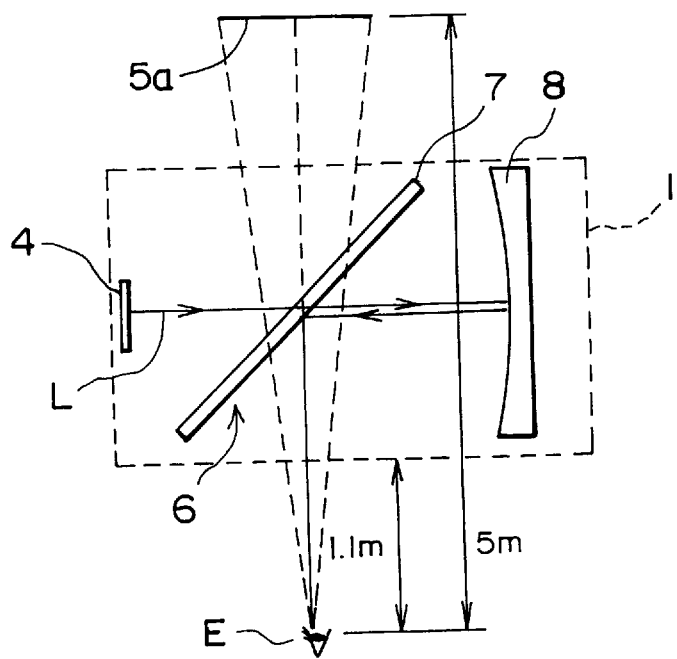
F I G . 2

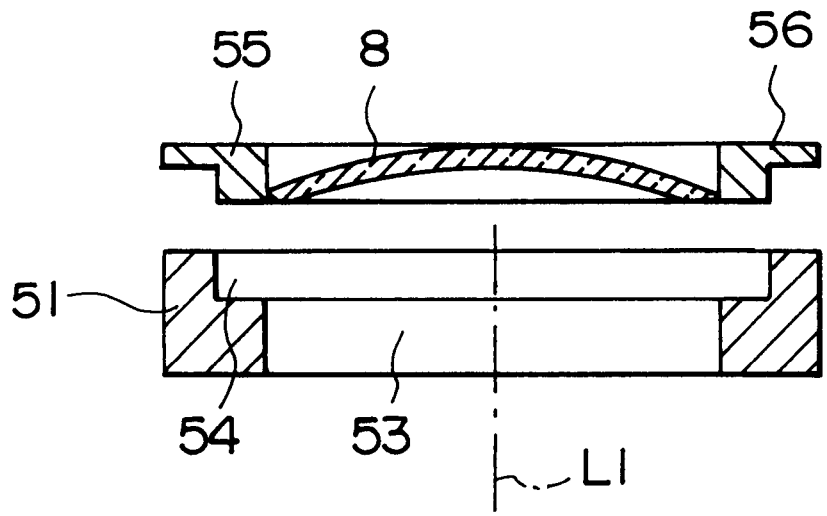
F I G . 10
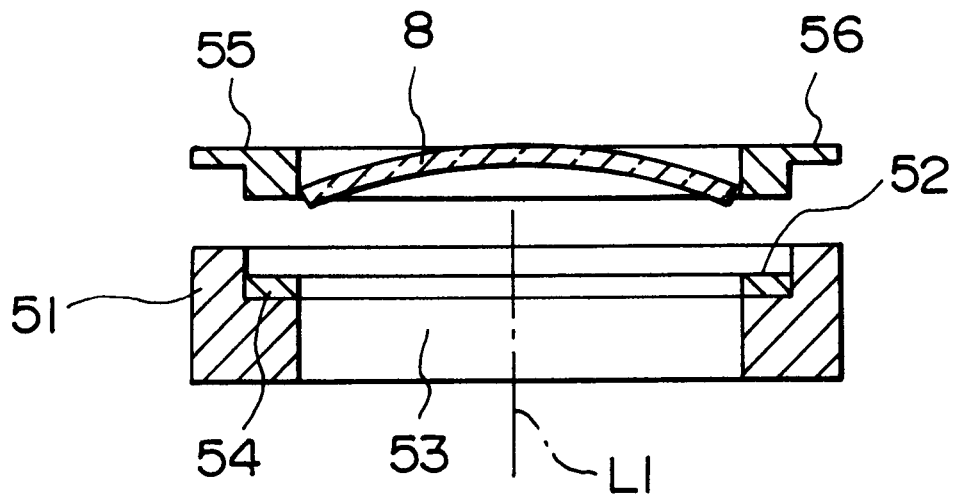
F I G . 11

APPARATUS FOR DISPLAYING VISUAL ACUITY CHART WITH CONSTANT MAGNIFICATION

BACKGROUND OF THE INVENTION

1. Field of the Invention

The present invention relates to an apparatus for displaying a visual acuity chart which displays visual chart images to an eye to be examined by using a half mirror and a concave mirror.

2. Description of Related Art

In conventional apparatus for displaying a visual acuity chart using a half mirror and a concave mirror, there are fixed distance apparatus in which visual chart images for an eye examination are displayed to an eye to be examined while the distance between the eye to be examined and the images is kept constant, and an infinity apparatus in which visual chart images for an eye examination are formed at infinity to be displayed to an eye to be examined.

However, the fixed distance apparatus for displaying a visual acuity chart has a problem, when the apparatus is placed in certain locations, for example, where an eye examination space is narrow. If a person to be examined cannot look at the visual charts from an appropriate position, an accurate eye examination cannot be carried out.

The infinity apparatus for displaying a visual acuity chart also has a problem. Although the freedom of locating the apparatus is high because parallel light beams are incident onto an eye to be examined from the visual charts, a visual acuity examination for the eye to be examined is normally carried out at an eye examination distance of 5 meters. As a result, differences in the adjusting power of the eye to be examined may occur to thereby cause excessive correction, and differences from a visual acuity value measured by other eye examination apparatus. Thus, an accurate eye examination can not be carried out as well.

SUMMARY OF THE INVENTION

The present invention provides apparatus for displaying a visual acuity charts to a person to be examined which can be used when the person is located at a selected viewing position separated from the apparatus by one a plurality of predetermined examination distances. The apparatus includes an apparatus body which houses a visual chart optical system for forming an image of a visual chart visible to the person to be examined located at the selected viewing position; and means for maintaining a constant forming magnification of the image of the visual chart formed by the optical chart optical system such that the size of the image of the visual chart appears the same for each of the predetermined examination distances. This results in the apparent distance between the person being examined and the visual chart image being constant, even though the apparatus may be used in circumstances where the actual distance between the person and the image are different, and increases the accuracy of examination results.

Thus, the present invention has been made in view of the above described circumstances, and an object of the present invention is to provide an apparatus for displaying a visual acuity chart capable of displaying images of visual charts to an eye to be examined at a constant distance irrespective of the dimensions (wide/narrow) of an eye examination space, so that an accurate eye examination can be carried out.

According to the present invention, there is provided an apparatus for displaying a visual acuity chart table comprising: an apparatus body; a visual chart optical system for forming an image of a visual chart provided in the visual acuity test table at a position apart from an eye to be examined by a desired distance; and means for keeping a constant forming magnification of the visual chart image of the visual chart formed by the visual chart optical system according to change of a distance between the eye to be examined and the apparatus body.

According to the present invention, there is provided an apparatus for displaying a visual acuity chart comprising: an apparatus body; a visual chart optical system, having a concave mirror which is movable in a desired optical axis direction, for forming an image of a visual chart provided in the visual acuity test table at a position apart from an eye to be examined by a desired distance; an optical member which is arrangeable in an optical path of the visual chart optical system; and means for moving the concave mirror of the visual chart optical system in a desired optical axis direction and arranging the optical member in the optical path of the visual chart optical system according to change of a distance between the eye to be examined and the apparatus body, to keep a constant forming magnification of the image of the visual chart.

According to the present invention, there is provided an apparatus for displaying a visual acuity chart comprising: a visual acuity chart plate on which a plurality of visual charts are provided; an illuminating system for illuminating each of the visual charts on the visual acuity chart plate with light; a visual chart optical system, having a concave mirror which is movable in a desired optical axis direction, for forming an image of each of the visual charts illuminated by the illuminating system at a position apart from an eye to be examined by a desired distance; an optical member which is arrangeable in an optical path of the visual chart optical system; and means for moving the concave mirror of the visual chart optical system in a desired optical axis direction and arranging the optical member in the optical path of the visual chart optical system according to change of a distance between the eye to be examined and the apparatus body, to keep a constant forming magnification of the image of the visual chart.

According to the present invention, the concave mirror is moved in the desired optical axis direction by arranging a spacer along the desired optical axis direction.

In the apparatus for displaying a visual acuity chart table of the present invention, as a result of the visual chart optical system having the concave mirror and the half mirror for forming the image of the visual chart provided on the visual acuity chart table at a predetermined distance from the eye to be examined, the forming magnification of the image is kept constant in response to the change of the distance between the eye to be examined and the apparatus body. The apparent size of the image is independent of the distance between the eye to be examined and the apparatus body. Thus, the visual chart image of having a constant size can be displayed to the eye to be examined and an accurate eye examination to the eye to be examined can be carried out irrespective of the dimensions of the eye examination space.

In the apparatus for displaying a visual acuity chart of the invention, the concave mirror of the visual chart optical system is moved in a desired optical axis direction and the optical member is arranged in the optical path of the visual chart optical system in response to the change of the distance between the eye to be examined and the apparatus body so that the forming magnification of the visual chart image is kept constant. Thus, similar to the above case of the apparatus for displaying a visual acuity chart of the invention, irrespective of the distance between the eye to be examined of a person to be examined and the apparatus body, the image of the visual chart has a constant size, when displayed to the eye to be examined and an accurate eye examination of the eye to be examined can be carried out irrespective of the dimensions of the eye examination space.

In the apparatus for displaying a visual acuity chart of the invention, the visual chart optical system having the half mirror and the concave mirror movable in a desired optical axis direction is used, and in response to the change of the distance between the eye to be examined and the apparatus body, the concave mirror of the visual chart optical system is moved in the desired optical axis direction and the optical member is arranged in the optical path of the visual chart optical system so that the forming magnification of images of the various kinds of visual charts on the circular arrangement illuminated by the illuminating system is kept constant. Thus, similar to the above case of the apparatus for displaying a visual acuity chart of the invention, irrespective of the distance between the eye to be examined of a person to be examined and the apparatus body, the images of the respective visual charts can be displayed to the eye to be examined and various and accurate eye examinations of the eye to be examined can be carried out irrespective of the dimensions of the eye examination space.

In the apparatus for displaying a visual acuity chart table of the invention, the concave mirror is moved in the desired optical axis direction by insertion or removal of the spacer along the optical axis direction of the visual chart optical system, so that, with the extremely simple structure and the simple operation, irrespective of the distance between the eye to be examined of a person to be examined and the apparatus body, the visual chart images having a constant size can be displayed to the eye to be examined and an accurate eye examination to the eye to be examined can be carried out irrespective of the dimensions of the eye examination space.

BRIEF DESCRIPTION OF THE DRAWINGS

FIG. 1 is a perspective view of an apparatus for displaying a visual acuity chart according to a first embodiment of the present invention;

FIG. 2 is a sectional view of the apparatus for displaying a visual acuity chart according to the first embodiment of the invention;

FIG. 10 is a sectional view of a receptive frame for changing the position of the concave mirror in the apparatus for displaying a visual acuity chart of the second embodiment of the invention; and FIG. 11 is a sectional view of the receptive frame and a spacer for changing the position of the concave mirror in the apparatus for displaying a visual acuity chart of the second embodiment of the invention.

DETAILED DESCRIPTION OF THE PREFERRED EMBODIMENTS

Embodiments of the present invention will be described in detail with reference to the drawings.

Embodiment 1

Figure 3:
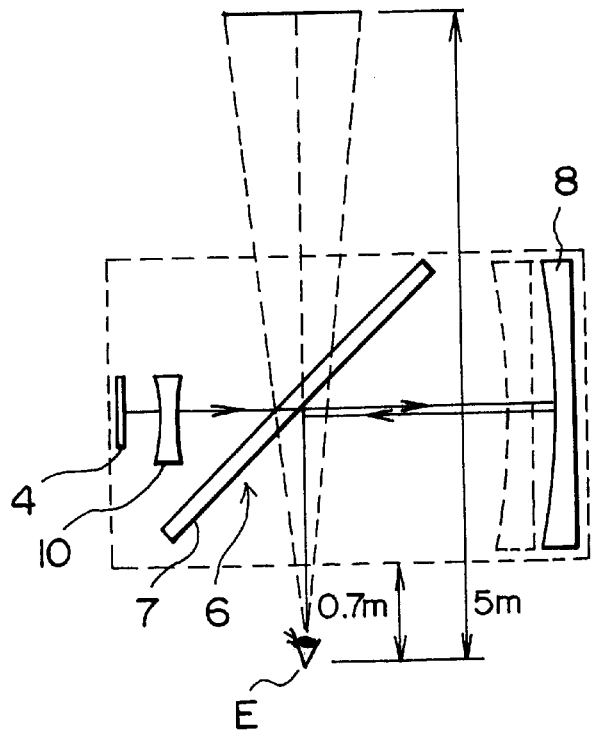
FIG. 3 is a sectional view of the apparatus for displaying a visual acuity chart according to the first embodiment of the invention in a case wherein the position of a concave mirror is changed and an auxiliary optical member is used.
Figure 4:
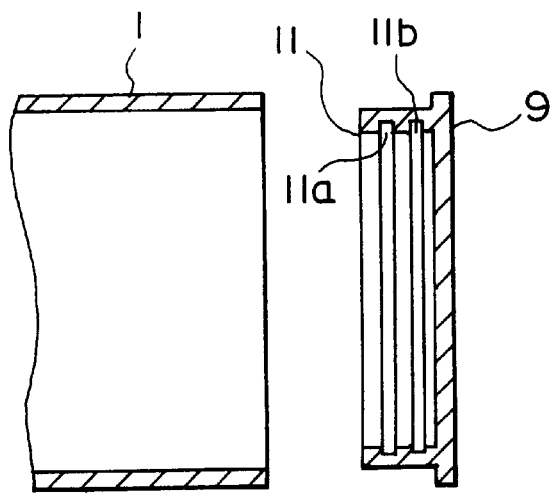
FIG. 4 is a sectional view of a grooved frame portion for a concave mirror used in the apparatus for displaying a visual acuity chart according to the first embodiment of the invention.
Figure 5A:
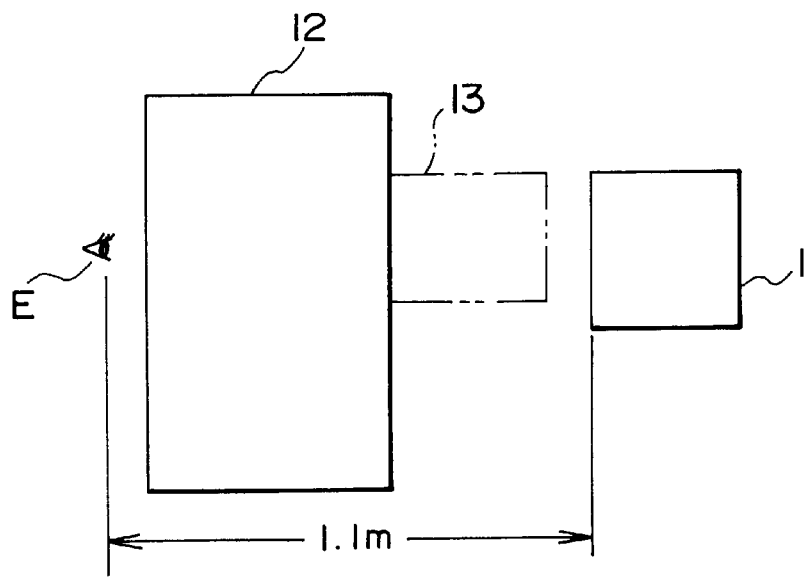
FIGS. 5A and 5B are upper views of the arrangement in a case wherein the apparatus for displaying a visual acuity chart of the first embodiment of the invention is used.
Figure 5B:
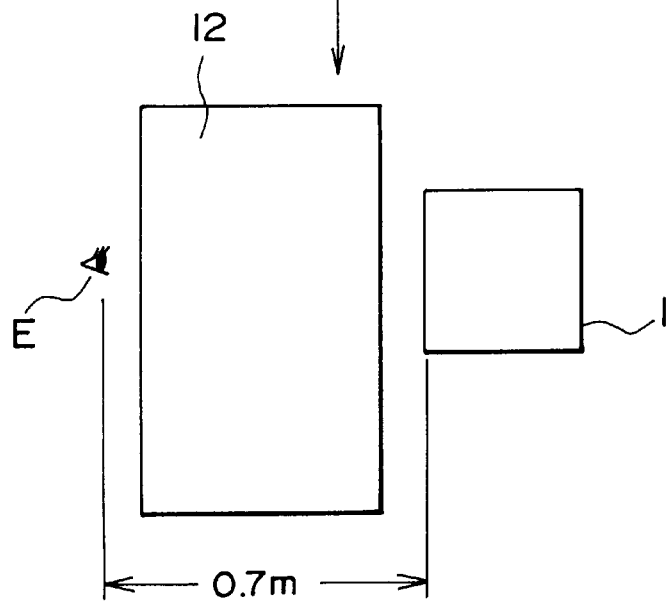

FIGS. 1 to 5B show an apparatus for displaying a visual acuity chart according to a first embodiment of the present invention, in which FIG. 1 is a perspective view of an apparatus for displaying a visual acuity chart according to a first embodiment of the present invention, FIG. 2 is a sectional view of the apparatus for displaying a visual acuity chart according to the first embodiment of the invention, FIG. 3 is a sectional view of the apparatus for displaying a visual acuity chart according to the first embodiment of the invention in a case wherein the position of a concave mirror is changed and an auxiliary optical member is used, FIG. 4 is a sectional view of a grooved frame portion for a concave mirror used in the apparatus for displaying a visual acuity chart according to the first embodiment of the invention, and FIGS. 5A and 5B are upper views of the arrangement in a case wherein the apparatus for displaying a visual acuity chart of the first embodiment of the invention is used.

The apparatus for displaying a visual acuity chart according to the first embodiment shown in FIGS. 1 to 3 includes an apparatus body 1 which has a rectangular parallelepiped shape and is provided with a square shaped opening 2 used for perception at one end surface thereof, a visual chart plate 4 which has a visual chart 5 such as a Landolt ring and is arranged inside the apparatus body 1. A visual chart optical system 6 is disposed inside the apparatus body for forming a visual image of the visual chart 5 at a position where an eye E to be examined of a person to be examined can see the image when facing sitting the apparatus body 1, that is, at a position where the eye to be examined can see the image by looking through the opening 2.

The visual chart optical system 6 includes a half mirror 7 which is arranged as a semi-transmitting mirror with an inclination of 45 degrees with respect to the direction of an optical axis and transmits a light beam from the visual chart 5 of the visual chart plate 4, a concave lens 10 to be inserted into or removed from the optical path between the visual chart plate 4 and the half mirror 7, (see FIG. 3) and a concave mirror 8 for reflecting the light beam transmitted by the half mirror 7 as a parallel light beam. The parallel light beam reflected by the concave mirror 8 is reflected by the half mirror 7 toward the eye E to be examined, so that the image of the visual chart 5 of the visual chart plate 4 is formed as a virtual image 5a at a position apart from the eye E to be examined by a desired distance (for example, 5 meters).

The position of the concave mirror 8 is adjustable along the direction of the optical axis L formed by the visual chart plate 4 and the half mirror 7. That is, as shown in FIG. 4, an attachable/detachable lid body 9 with respect to the apparatus body 1 is provided at an end portion of the apparatus body 1 at the side of the concave mirror 8. A grooved frame 11 having, for example, two substantially semicircular grooves 11a and 11b orthogonal to the direction of the optical axis L is provided in the lid body 9, so that the concave mirror 8 can be arranged in either one of the grooves 11a and 11b in the state where the lid body 9 is detached from the apparatus body 1.

Note that, FIG. 2 shows the state in which the lid body 9 with the concave mirror 8 arranged in the groove 11a is attached to the apparatus body 1, and FIG. 3 shows the state in which the lid body 9 with the concave mirror 8 arranged in the groove 11b is attached to the apparatus body 1.

In the arrangement of the concave mirror 8 as shown in FIG. 2, the virtual image 5a is formed at an apparent distance of 5 meters from the eye E to be examined in the state in which the actual distance between the eye E to be examined and the apparatus for displaying a visual acuity chart table is 1.1 meters. In the arrangement of the concave mirror 8 as shown in FIG. 3, when the concave lens 10 is inserted in the optical path of the optical axis L, the virtual image 5a is formed at an apparent distance of 5 meters from the eye E to be examined in the state in which the actual distance between the eye E to be examined and the apparatus for displaying a visual acuity chart table is 0.7 meters. Thus, irrespective of the distance between the eye E to be examined and the apparatus body 1, the forming magnification of visual chart images of visual charts can be kept constant.

According to the apparatus for displaying a visual acuity chart of the first embodiment, by a simple operation of arranging the concave surface mirror 8 in one of the grooves 11a and 11b and inserting or removing the concave lens 10 from the optical path of the optical axis L, irrespective of the distance between the eye E to be examined and the apparatus body 1, the image of the visual chart 5 can be formed as the virtual image 5a at a constant apparent distance of, for example, 5 meters from the eye E to be examined by the visual chart optical system 6. As a result, as shown in FIGS. 5A and 5B, the apparatus for displaying a visual acuity chart table of the first embodiment can be applied to both of the case (corresponding to the state shown in FIG. 2) where an eye examination is carried out at a distance of 1.1 meters from the apparatus body 1 to the eye E to be examined so that a lens containing drawer 13 containing a large number of eye examination lenses in an eye examination table 12 can be drawn, and the case (corresponding to the state shown in FIG. 3) where an eye examination is carried out at a distance of 0.7 meters from the apparatus body 1 to the eye E to be examined while the lens containing drawer 13 is not used in relation to an eye examination space but the apparatus body 1 is placed close to the eye examination table 12.

Embodiment 2

An apparatus for displaying a visual acuity chart according to a second embodiment will be described with reference to FIGS. 6 to 11.

Figure 6:
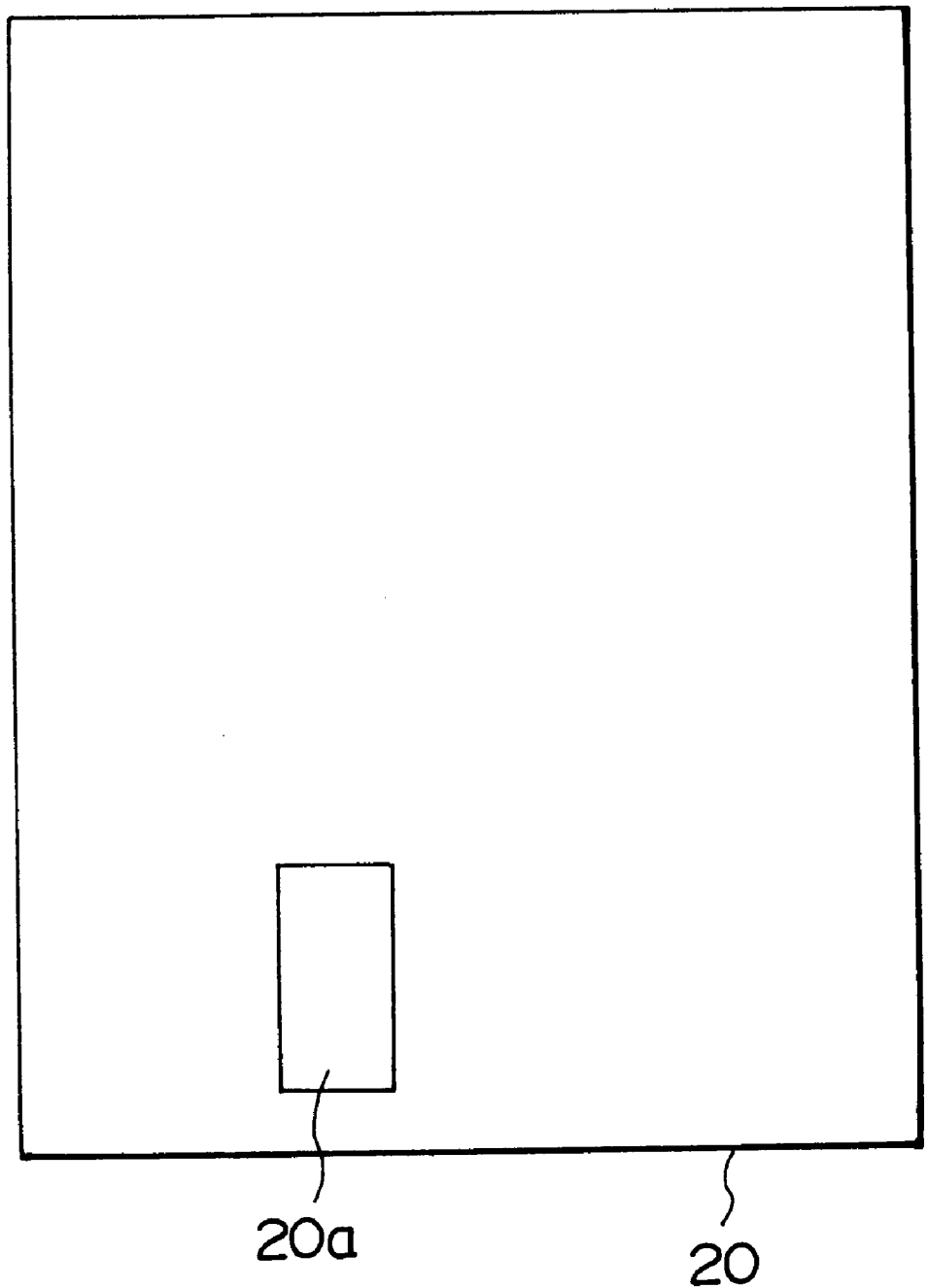
FIG. 6 is a side view of an apparatus for displaying a visual acuity chart of a second embodiment of the invention.
Figure 7:
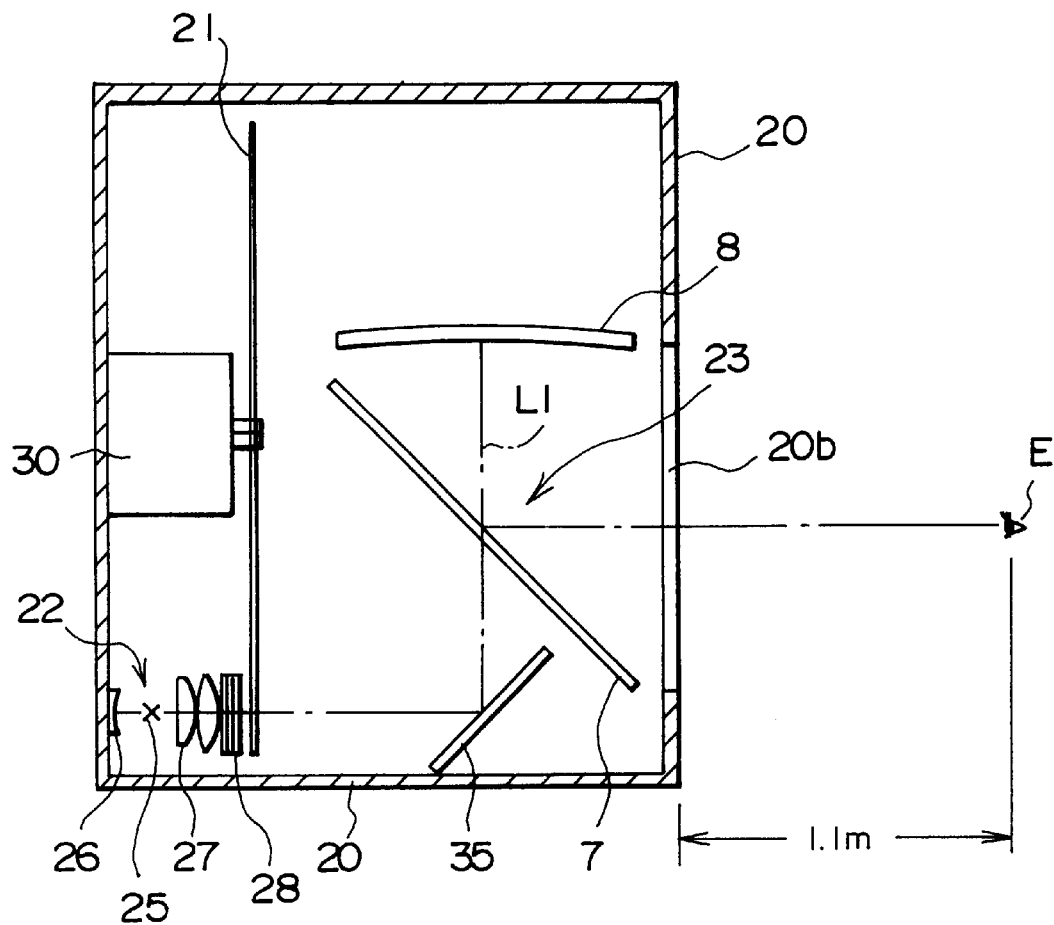
FIG. 7 is a sectional view of the apparatus for displaying a visual acuity chart of the second embodiment of the invention.
Figure 8:
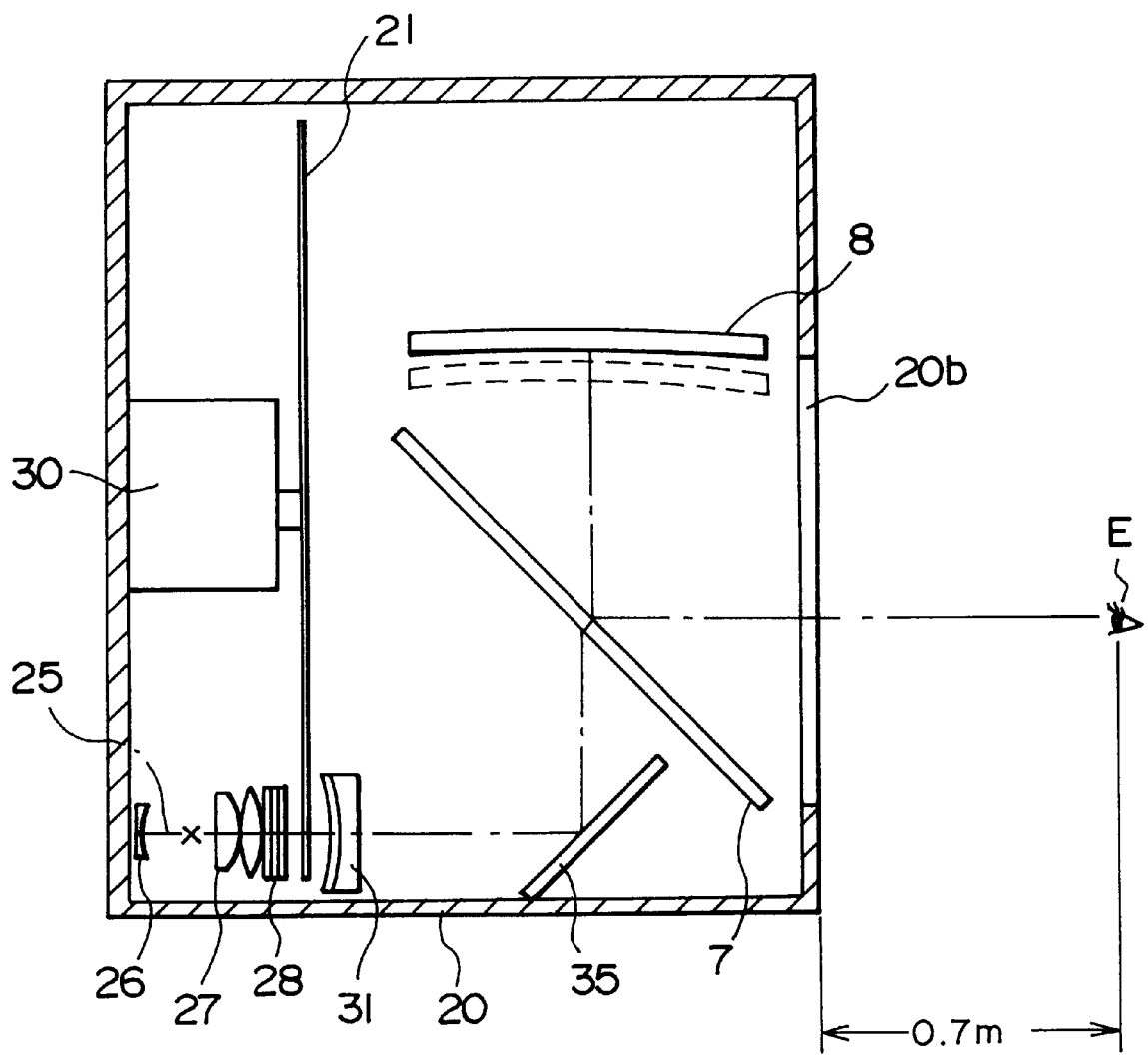
FIG. 8 is a sectional view of the apparatus for displaying a visual acuity chart of the second embodiment in a case wherein the position of a concave mirror is changed and an auxiliary optical member is used.
Figure 9:
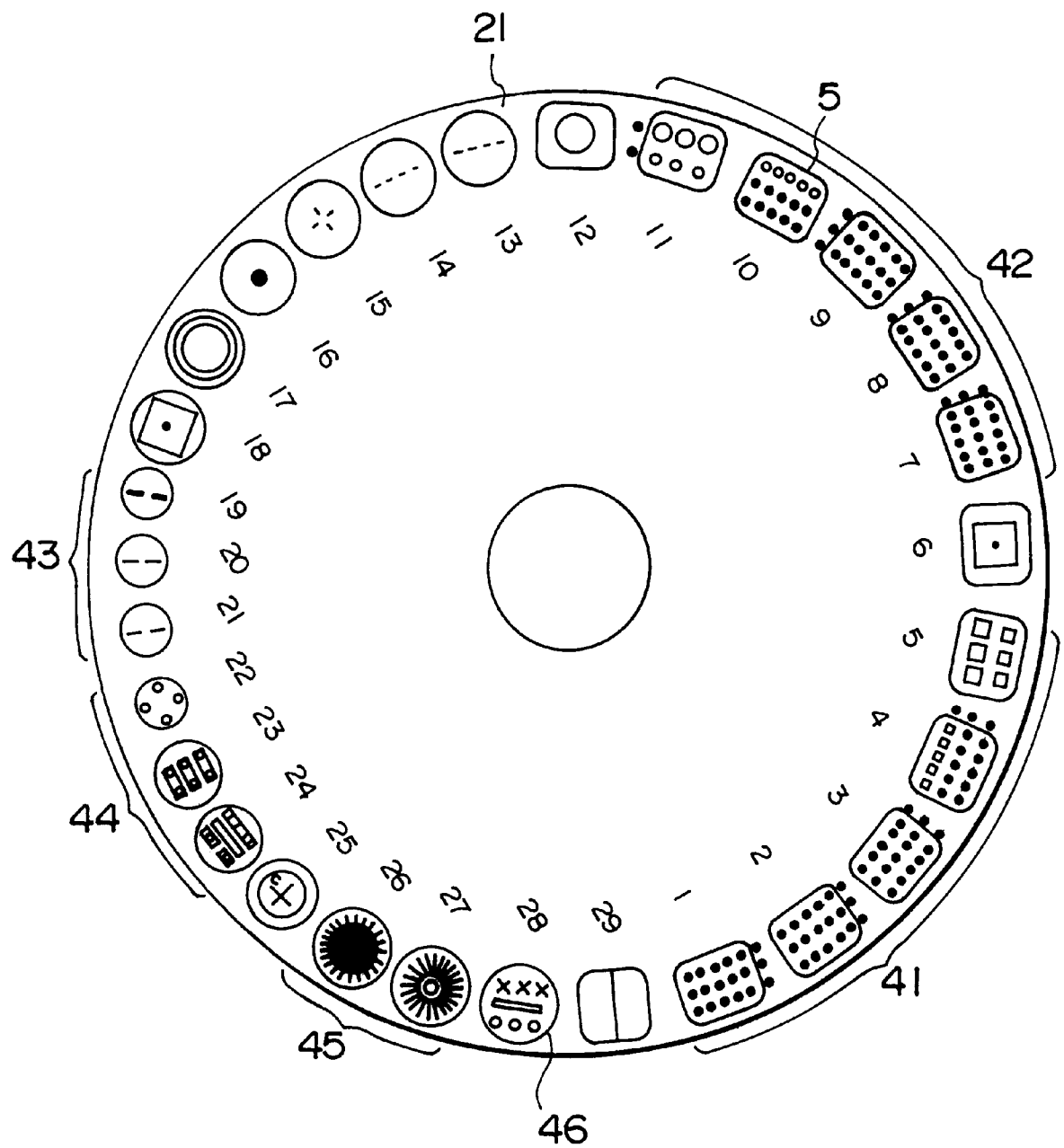
FIG. 9 is a schematic front view of a rotational plate provided with various kinds of visual charts used in the apparatus for displaying a visual acuity chart of the second embodiment of the invention.

FIG. 6 is a side view of an apparatus for displaying a visual acuity chart of a second embodiment of the invention, FIG. 7 is a sectional view of the apparatus for displaying a visual acuity chart of the second embodiment of the invention, FIG. 8 is a sectional view of the apparatus for displaying a visual acuity chart of the second embodiment in a case wherein the position of a concave mirror is changed and an auxiliary optical member is used, FIG. 9 is a schematic front view of a rotational plate provided with various kinds of visual charts used in the apparatus for displaying a visual acuity chart of the second embodiment of the invention, FIG. 10 is a sectional view of a receptive frame for changing the position of the concave mirror in the apparatus for displaying a visual acuity chart of the second embodiment of the invention, and FIG. 11 is a sectional view of the receptive frame and a spacer for changing the position of the concave mirror in the apparatus for displaying a visual acuity chart of the second embodiment of the invention.

As shown in FIG. 7, The apparatus for displaying a visual acuity chart table according to the second embodiment includes a rotating plate (visual acuity chart plate) 21 on which various kinds of visual charts including the visual chart 5 for an eye examination are circularly arranged so as to transmit light through the respective ones. The plate 1 is rotated by a driving motor 30, an illumination system 22 for illuminating the respective visual charts on the rotational plate 21 with illumination light, and a visual chart optical system 23 for forming visual chart images of the respective visual charts on the rotating plate 21 at an apparent distance of 5 meters from the eye E to be examined are also disposed in the apparatus body 20.

The illumination system 22 includes a light source lamp 25, a reflective mirror 26, a collective lens system 27, and a filter 28. The light generated in the light source lamp 25 is reflected by the reflective mirror 26, so that the reflected light illuminates to a visual chart on the rotating plate 21 through the collective lens system 27 and the filter 28.

The visual chart optical system 23 includes a reflective mirror 35, the half mirror 7, and the concave mirror 8. The position of the concave mirror 8 is adjustable in the direction of an optical axis L1. Light beams from the visual chart illuminated by the illumination system 22 are reflected by the reflective mirror 35 and then are projected onto the eye E to be examined by the half mirror 7 and the concave mirror 8, so that visual chart images of the various kinds of visual charts including the visual chart 5 are formed as virtual images at an apparent distance of 5 meters from the eye E to be examined.

Note that, as shown in FIG. 8, a concave lens 31 as an auxiliary optical member is arranged in the optical path of the visual chart optical system 23 such that the concave lens 31 can be inserted into and removed from the optical path.

Insertion or removal of the concave lens 31 into or from the optical path of the visual chart optical system 23 is performed in such a manner that, as shown in FIG. 6, for example, an opening and closing lid 20a which can be opened and closed is provided in a wall plate of the apparatus body 20, the opening and closing lid 20a is opened, and the concave lens 31 is inserted into or removed from the optical path in the vicinity of the rotating plate 21.

Then, the visual chart optical system 23 realizes the state as shown in FIG. 7 in which the distance between the eye E to be examined and the apparatus body 20 is 1.1 meters and the apparent distance between the eye E to be examined and the virtual image of the visual chart is 5 meters. Also, by insertion of the concave lens 31 into the optical path of the visual chart optical system 23 and adjustment of the position of the concave mirror 8, the visual chart optical system 23 realizes the state as shown in FIG. 8 in which the distance between the eye E to be examined and the apparatus body 20 is 0.7 meters and the apparent distance between the eye E to be examined and the virtual image of the visual chart is 5 meters. Note that an opening portion 20b for perception of the eye E to be examined is provided in the apparatus body 20.

As shown in FIG. 9, the rotating plate 21 is provided with a hiragana (i.e. Japanese character) visual chart group 41, a Landolt ring visual chart group 42 including the visual chart 5, a visual chart group 43 for a polarization test, a visual chart group 44 for a red/green test, a visual chart group 45 for an astigmatism test, a stereoscopic visual chart 46, and the like.

FIGS. 10 and 11 show a specific structure of a receptive frame 51 and a spacer 52 for adjusting the position of the concave mirror 8 of the apparatus body 20 along the direction of the optical axis L1. The receptive frame 51 includes a through hole 53 through which light can transmit in the center portion thereof and a concave receptive portion 54. The frame 51 is fixed inside the apparatus body 20 so that the optical axis L1 passes through the center of the through hole 53. An annular mirror holder 55 having a flange portion 56 and the concave lens 8 provided thereon is directly attached to the receptive frame 51 as shown in FIG. 10, or is attached to the receptive frame 51 through the annular spacer 52 with a predetermined thickness as shown in FIG. 11, whereby realizing the state in which the distance between the eye E to be examined and the apparatus body 20 is 1.1 meters as shown in FIG. 7 and the state in which the distance between the eye E to be examined and the apparatus body 20 is 0.7 meters as shown in FIG. 8.

In the apparatus for displaying a visual acuity chart according to the second embodiment, in response to the change of the distance between the eye E to be examined and the apparatus body 20, the concave mirror 8 of the visual chart optical system 23 is moved in the optical axis direction and the concave lens 31 is inserted into the optical path of the visual chart optical system 23, so that the forming magnification of the images of various kinds of visual charts on the circular arrangement illumination by the illumination system 22 is kept constant. Thus, irrespective of the distance between the eye E to be examined of a person to be examined and the apparatus body 20, the visual chart images of the respective visual charts can be displayed to the eye E to be examined at a constant size, and various and accurate eye examinations to the eye E to be examined can be carried out irrespective of the dimensions of an eye examination space.

In the second embodiment, although the concave lens 31 as the auxiliary optical member is inserted into the vicinity of the rotating plate 21, the position of insertion of the concave lens 31 is not specifically restricted as long as the position of insertion is in the optical path of the visual chart optical system.

Also, in the second embodiment, although the concave lens 31 is used as the auxiliary optical member, even if a convex lens is used, irrespective of the distance between the eye E to be examined of a person to be examined and the apparatus body 20, the forming magnification of visual chart images of various kinds of visual charts can be kept constant.

As described above, according to the present invention, irrespective of the distance between the eye to be examined of a person to be examined and the apparatus body, visual chart images having a constant size can be displayed to the eye to be examined, so that the apparatus for displaying a visual acuity chart capable of carrying out an accurate eye examination to the eye to be examined irrespective of the dimensions of an eye examination space can be provided.

According to the present invention, irrespective of the distance between the eye to be examined of a person to be examined and the apparatus body, the respective visual chart images of the respective visual charts can be displayed to the eye to be examined, so that the apparatus for displaying a visual acuity chart capable of carrying out various and accurate eye examinations to the eye to be examined irrespective of the dimensions of an eye examination space can be provided.

According to the present invention, irrespective of the distance between the eye to be examined of a person to be examined and the apparatus body, with the extremely simple structure and simple operation, visual chart images having a constant size can be displayed to the eye to be examined, so that the apparatus for displaying a visual acuity chart table capable of carrying out an accurate eye examination to the eye to be examined irrespective of the dimensions of an eye examination space can be provided.

What is claimed is:

1. An apparatus for displaying a visual acuity chart to a person to be examined, said person being located at a selected viewing position separated from the apparatus by one of a plurality of predetermined examination distances, comprising:

an apparatus body;

a visual chart optical system for forming an image of a visual chart visible to the person to be examined located at the selected viewing position; and means for maintaining a constant forming magnification of the image of the visual chart formed by the visual chart optical system such that the size of the image of the visual chart appears the same for each of the predetermined examination distances.

2. The apparatus according to claim 1 wherein the visual chart optical system has a half mirror and a concave mirror.

3. An apparatus for displaying a visual acuity chart to a person to be examined, said person being located at a selected viewing position separated from the apparatus by one of a plurality of predetermined examination distances, comprising:

an apparatus body;

a visual chart optical system, having a concave mirror which is moveable in an optical axis direction, for forming an image of an visual chart;

an optical member which is arrangeable in an optical path of the visual chart optical system; and means for moving the concave mirror of the visual chart optical system in the optical axis direction and arranging the optical member in the optical path of the visual chart optical system at a position associated with the selected viewing position to keep a constant forming magnification of the visual chart image of the visual chart such that the size of the image of the visual chart appears the same for each of the predetermined examination distances.

4. The apparatus according to claim 3 wherein the concave mirror is moved in the optical axis direction by arranging a spacer along the optical axis direction.

5. The apparatus according to claim 3 wherein the optical member is one of a concave lens and a convex lens.

6. An apparatus for displaying a visual acuity chart to a person to be examined, said person being located at a selected viewing position separated from the apparatus by one a plurality of predetermined examination distances, comprising:

a visual acuity chart plate on which a plurality of visual charts are provided;

an illuminating system for illuminating a visual chart on the visual acuity chart plate with light;

a visual chart optical system, having a concave mirror which is moveable in a optical axis direction, for forming an image of the visual chart illuminated by the illuminating system;

an optical member which is arrangeable in an optical path of the visual chart optical system; and means for moving the concave mirror of the visual chart optical system in the optical axis direction and arranging the optical member in the optical path of the visual chart optical system at a position associated with the selected viewing position to keep a constant forming magnification of the image of the visual chart such that the size of the image of the visual chart appears the same for each of the predetermined examination distances.

7. The apparatus according to claim 6 wherein the concave mirror is moved in the optical axis direction by arranging a spacer along the optical axis direction.

8. The apparatus according to claim 6 wherein the optical member is one of a concave lens and a convex lens.

* * * * *